US008622923B2

(12) United States Patent
Pons et al.

(10) Patent No.: US 8,622,923 B2
(45) Date of Patent: Jan. 7, 2014

(54) SELF-CALIBRATING PRESSURE SENSOR

(75) Inventors: Patrick Pons, Escalquens (FR); Pierre Montoriol, Monremont (FR); Pierre Yameogo, Toulouse (FR)

(73) Assignees: CAPTOMED EURL, Labege (FR); Centre National de la Recherche Scientifique (CNRS), Paris (FR)

( * ) Notice: Subject to any disclaimer, the term of this patent is extended or adjusted under 35 U.S.C. 154(b) by 1006 days.

(21) Appl. No.: 12/181,392

(22) Filed: Jul. 29, 2008

(65) Prior Publication Data
US 2009/0036754 A1 Feb. 5, 2009

(30) Foreign Application Priority Data

Jul. 31, 2007 (FR) ...................................... 07 05573

(51) Int. Cl.
*A61B 5/03* (2006.01)

(52) U.S. Cl.
USPC .......................................................... 600/561

(58) Field of Classification Search
USPC ......................................... 600/561, 544, 407
See application file for complete search history.

(56) References Cited

U.S. PATENT DOCUMENTS

| | | | | |
|---|---|---|---|---|
| 3,920,002 A * | 11/1975 | Dye et al. | ...................... | 600/561 |
| 4,088,917 A * | 5/1978 | Martin et al. | .................. | 310/357 |
| 4,281,991 A * | 8/1981 | Michl et al. | .................... | 523/115 |
| 4,407,296 A * | 10/1983 | Anderson | ...................... | 600/488 |
| 4,418,326 A * | 11/1983 | Delapierre | ........................ | 338/5 |
| 4,465,075 A * | 8/1984 | Swartz | ............................ | 600/485 |
| 4,468,639 A * | 8/1984 | Green et al. | ................... | 333/153 |
| 4,685,469 A * | 8/1987 | Keller | ............................ | 600/561 |
| 4,703,757 A * | 11/1987 | Cohen | ............................ | 600/480 |
| 4,812,742 A * | 3/1989 | Abel et al. | ...................... | 324/537 |
| 4,951,671 A * | 8/1990 | Coan | .............................. | 600/405 |
| 5,019,977 A * | 5/1991 | LaPointe et al. | .................. | 702/3 |
| 5,184,619 A * | 2/1993 | Austin | ........................... | 600/376 |
| 5,437,284 A | 8/1995 | Trimble | | |
| 5,564,434 A * | 10/1996 | Halperin et al. | .............. | 600/488 |
| 5,810,734 A * | 9/1998 | Caro et al. | ...................... | 600/561 |
| 5,951,487 A * | 9/1999 | Brehmeier-Flick et al. | .. | 600/561 |
| 6,010,461 A * | 1/2000 | Haniff et al. | ................... | 600/561 |
| 6,111,520 A * | 8/2000 | Allen et al. | ............... | 340/870.16 |
| 6,394,986 B1 * | 5/2002 | Millar | ........................... | 604/264 |
| 6,423,001 B1 * | 7/2002 | Abreu | ........................... | 600/561 |
| 6,450,972 B1 * | 9/2002 | Knoll | ............................. | 600/561 |
| 6,475,170 B1 | 11/2002 | Doron et al. | | |
| 6,706,001 B2 * | 3/2004 | Fresco | .......................... | 600/585 |
| 6,976,964 B2 * | 12/2005 | Chevallet et al. | ............. | 600/486 |
| 7,209,788 B2 * | 4/2007 | Nicolelis et al. | ................ | 607/48 |
| 7,245,738 B2 * | 7/2007 | Pribyl | ........................... | 381/396 |

(Continued)

FOREIGN PATENT DOCUMENTS

WO 2006/073770 A1 7/2006

*Primary Examiner* — Max Hindenburg
*Assistant Examiner* — Jonathan M Foreman
(74) *Attorney, Agent, or Firm* — Young & Thompson

(57) ABSTRACT

A self-calibrating device for measuring intracorporeal pressure, includes:
  A pressure sensor having i) a test body (11) of which a segment of smaller thickness constitutes a membrane that can deform under the action of the pressure of the medium, the membrane being equipped with at least one piezoelectric transducer that can translate a mechanical stress into an electrical signal, and ii) a polarization contact,
  An actuator that is connected to a voltage source, having a non-deformable base, whereby at least one surface of the actuator is polarizable, the pressure sensor being placed above the actuator so that the membrane is in vertical alignment with the polarizable surface (22).

19 Claims, 2 Drawing Sheets

(56) References Cited

U.S. PATENT DOCUMENTS

| | | | |
|---|---|---|---|
| 2002/0042565 A1* | 4/2002 | Cooper et al. | 600/407 |
| 2004/0073137 A1* | 4/2004 | Lloyd et al. | 600/561 |
| 2005/0288722 A1* | 12/2005 | Eigler et al. | 607/9 |
| 2006/0104870 A1* | 5/2006 | Rumps et al. | 422/130 |
| 2006/0107749 A1 | 5/2006 | Liu et al. | |
| 2006/0231943 A1* | 10/2006 | Chiu et al. | 257/700 |
| 2006/0241354 A1* | 10/2006 | Allen | 600/561 |
| 2007/0255166 A1* | 11/2007 | Carney et al. | 600/561 |
| 2008/0000511 A1* | 1/2008 | Kuroyanagi et al. | 136/201 |

* cited by examiner

SELF-CALIBRATING PRESSURE SENSOR

BACKGROUND OF THE INVENTION

This invention belongs to the field of pressure sensors and more particularly sensors designed for monitoring the intracorporeal pressure of a patient during a period of medical surveillance, in particular during a surgical intervention.

Its object is a self-calibrating device for measuring intracorporeal pressure, combining a sensor with a piezoelectric transducer that reacts under the action of pressure and an actuator that makes it possible to produce, by specified amplitude polarization, a calibrated deformation at the level of the sensor.

The pressure measurements are commonly used to judge the state of vital physiological functions, or the gravity of a trauma, a pathology that produces abnormally high compression of an organ. These measurements of pressure, in particular arterial pressure and intracranial pressure, are taken daily in emergency services, in particular in intensive care.

The measurement of arterial pressure is necessary in numerous situations such as states of shock not responding in the first hour to medical management (septic shock, cardiogenic shock), refractory convulsive status epilepticus or acute respiratory distress syndrome. The post-operative management of multiple situations such as renal grafting, major orthopedic surgery, or major digestive surgery, where extended intervention requires many volume infusions that can lead to difficult post-operative hemodynamic management, also requires close monitoring of arterial pressure.

The measurement of the intracranial pressure is indicated in neuro-traumatology in cases of serious cranial traumas and also in certain cases of relational cerebral edemas, meningeal hemorrhages or aggressively growing cerebral tumors. All of these pathological processes have in common the development, by the action of mass, of intracranial hypertension, since the cranium cannot be expanded in an adult. An increase in the intracranial pressure produces a reduction of the cerebral perfusion pressure that may be responsible for a decrease in the cerebral blood flow and for creating an energy threat situation that can lead to ischemia, i.e., the death of the cerebral tissue.

It is understood that the monitoring and regulation of the intracorporeal pressure can assume an often vital importance of the first order in contexts that are particularly difficult for the practitioners. Means for measuring both the intracranial pressure as well as the arterial pressure have therefore been sought for a long time—means that are suitable during work in an operating room or in a medical environment, requiring tools that are compact and easy to handle and that can provide reliable information continuously and under strict sanitization conditions.

In a conventional way, the measurement of arterial pressure is taken using a sensor that is inserted into the radial or femoral artery by means of a catheter. The principle of the sensor is that of a membrane that is coupled to gauges with resistors placed on a Wheatstone bridge. The resistance variations due to the compression or to the extension of gauges connected to the membrane are transformed into an electrical signal that is proportional to the arterial pressure. The resistors can be replaced by a system that induces a variation of an electromagnetic coupling based on movements of the membrane. The sensor can be external, which presents various drawbacks linked to the removal of the sensor, in particular in connection with effects of damping and deformation of the pressure signal and a limitation of the frequency response.

Integrated pressure sensors in the implanted end of a catheter are also used increasingly frequently, in particular in an operating room. Since 1980, sensors based on fiber-optic or piezoelectric transducer technologies (in particular with piezoresistive gauges) made of silicon have commonly been used. The gauge components are encapsulated at the end of a catheter made of nylon with an overall diameter that varies from 1.17 mm to 2.67 mm for the commercialized models. Owing to the miniaturization of the measuring probe, it has been possible to limit the risks of thrombosis during the taking of the arterial pressure, and the trauma linked to the intracranial implantation of the sensor has been minimized. Thus, in recent years, these devices have made it possible to measure the arterial pressure and the intracranial pressure at a lower cost, in a routine manner, with a much better precision of measurements, a reduced invasive nature and better controlled septic risks.

The fact remains that these techniques still exhibit drawbacks and call for innovations. A major problem with silicon-gauge sensors and especially with sensors with actual optical fibers is their tendency to drift, regardless of conditions of storage and use. Values of 2 to 5 mm of Hg per 24-hour cycles are commonly observed. It is therefore essential to carry out a re-calibration at regular intervals. At present, however, the calibration is carried out only in an extracorporeal manner, which very seriously increases the risks of infection for the patients.

Actually, the calibration of the pressure sensors is in general carried out by applying a known pressure on the membrane of the sensor and by verifying that the electrical quantity delivered by the latter is equivalent to the stress exerted. In practice, whereby the sensors that are used in the medical medium deliver a pressure value that is equal to the difference between the measured pressure and the atmospheric pressure, a sensor is calibrated at atmospheric pressure: if it is correctly calibrated, the measured pressure should be zero when it is held in the open air or immersed in a small volume of sterile water.

The handling of an instrument that is placed in the body, then withdrawn and inserted again is, however, delicate by nature and the source of infectious complications whose consequences may prove extremely serious. For the measurement of the intracranial pressure in particular, the emergence of the physical, electrical or optical link with the outside medium at the level of the scalp is always a critical point. It is a possible septic entryway to the intradural medium, which is completely vulnerable to infection. The periodically repeated installation of a piece of equipment therefore significantly multiplies the risks of infection. Thus, because of a high septic risk, it is preferable that a placed sensor no longer be withdrawn to undergo periodic re-calibrations.

BRIEF SUMMARY OF THE INVENTION

The object of this invention is to provide a response to the above-mentioned drawbacks by proposing a pressure sensor whose drift over time can be easily monitored and corrected. Another object of the invention is to provide a pressure sensor that can be used for intracorporeal measurements, able to be calibrated in situ. These objectives involve miniaturization, reliability, and sensitivity of the device.

This invention responds to these objectives by proposing a self-calibrating device for measuring the intracorporeal pressure, comprising:

A pressure sensor that comprises i) a test body of which a segment of smaller thickness constitutes a membrane that can deform under the action of the pressure of the medium, whereby said membrane is equipped with at least one piezoelectric transducer that can translate a mechanical stress into an electrical signal, and ii) a polarization contact, An actuator that is connected to a voltage source, comprising a non-deformable base, whereby at least one surface of said actuator can be polarized, whereby said pressure sensor is placed above said actuator so that the membrane is in vertical alignment with of the polarizable surface.

In the device that is the object of the invention, a sensor and an actuator are therefore combined. For the sake of simplicity, it is considered in this description that the sensor is placed above the actuator, although it is only a matter here of a relative position between these two elements that can operate fully regardless of their position in space. It is recalled that a sensor is an element that converts a physical quantity into an electrical quantity. An actuator is an element that converts an electrical quantity into a physical (non-electrical) quantity. In this case, the actuator is able to transform an electrical voltage into an electrostatic force that creates a deformation. The latter is undergone by the sensor that transforms it into an electrical signal.

The first part of the device according to the invention is a pressure sensor, which can be of the type of pressure sensors with piezoelectric transducers that are already known per se. The operation of these sensors is based on the reaction of piezoreistant transducers (also called strain gauges) that are inserted into a membrane that deforms under the action of a pressure, whose resistance variation mirrors their inherent deformation and therefore the deformation of the test body on which they are installed.

The sensor therefore primarily consists of a test body that is responsible for transferring the pressure that is applied to it (by deformation of its surface due to an external pressure to be measured or to the electrostatic force that is generated upon the occasion of the calibration), on which a fine membrane is formed. It is possible to produce it, for example, using micromachining techniques used in microelectronics. Piezoelectric transducers, also produced using known microelectronic techniques, can then be used in the most suitable zones. The variations of their electrical characteristics transfer any movement or deformation of the membrane.

The sensor also comprises a polarization contact, such that when the actuator is charged, an electrostatic force can be exerted on the sensitive membrane.

The sensor is combined with an actuator that comprises a non-deformable base. The latter is connected to a voltage source, and at least one of its surfaces can be polarized. It is responsible for creating a known deformation of the membrane by electrical polarization. For this purpose, the pressure sensor is placed opposite said actuator so that the membrane of the sensor is directly above the polarizable surface of the actuator.

Actually, an electrostatic force can be generated when two parallel conductive surfaces are placed opposite one another and a potential difference is applied to them. The force that attracts or repels the electrodes (based on the sign of the voltage that is applied to them) can be approximated by the following equation:

$$F = \frac{\varepsilon \times S}{2d^2} \times U^2$$

in which $\varepsilon$ is the permittivity of the medium, S represents the surface of electrodes placed opposite one another, d is the distance between the electrodes, and U is the voltage applied to the electrodes.

In this application, the membrane of the pressure sensor acts as a first electrode, whereby the polarizable surface of the actuator constitutes the second electrode. By positioning a non-deformable conductive electrode at the base of the sensitive membrane, an electrostatic actuator is created that makes it possible to apply a force on the membrane and thus to deform it. This deformation is transformed by the piezoelectric transducers into electrical signals. For predetermined values of S, d, and $\varepsilon$, whereby the voltage U that is applied between the electrode and the membrane is known, the deflection undergone by the membrane is known. Whereby this deflection is equivalent to that obtained by the application of a given pressure, the electrical signal provided by the sensor is proportional to this pressure, which thus constitutes a calibration pressure from which the values of the intracorporeal pressure measured by the sensor can be rectified.

Using this device, it is possible to apply as required a known constraint to the membrane of the sensor, coming to apply a known pressure to the sensor, by means of the actuator that is combined with the sensor. The sensor can thus be calibrated—as often as needed without it being necessary to remove it from the medium in which it is placed—by a periodic charging of the device according to the invention.

According to an advantageous characteristic of the device that is the object of the invention, the sensor is kept above the actuator by a rigid connection, whereby the space encompassed between the membrane and the polarizable surface constitutes a cavity of specified size: the distance d between the electrodes is thus fixed. A monolithic device with an on-board actuator is then used where its reduced size makes it able to be inserted into a living organism by means of a catheter or the like.

According to another characteristic of the device according to the invention, the actuator comprises insulating means that separate the polarizable surface from the test body. The actuator can be equipped with an insulating element that separates it from the polarizable surface and the test body, or can itself be produced according to a structure and in a material that ensures the insulating function, as it will appear below. In particular, the rigid connection should not allow the electric current to pass.

In a variant embodiment of the device according to the invention, the actuator comprises, on a non-deformable insulating substrate, a metal electrode that is connected to a voltage source. This metal electrode constitutes a polarizable surface of the actuator, placed at the base of the membrane, and it is used as an electrostatic actuator that makes it possible to generate a known deformation of the membrane. The production of the electrode can be carried out by various processes, for example by one of the processes that is already used for the production of capacitive pressure sensors. In practice, the metal electrode consists of a metal layer that covers the substrate at least on the surface and that is found at the base of the membrane.

The insulating substrate can advantageously consist of a material that is selected from among glass, borosilicate glass, vitreous ceramic, and insulating silicon. Any other insulating material that has the required rigidity properties can be used.

According to an alternate variant of implementation of the invention, the actuator comprises a non-deformable conductive substrate that is connected to a voltage source and separated from the test body by at least one insulating element.

In this case, the conductive substrate is preferably made of conductive silicon while said at least one insulating element is a silicon oxide.

Regardless of the embodiment of the actuator combined with the pressure sensor, the test body and the membrane of said sensor are made of a conductive material, preferably silicon. For their production, it is possible to use, for example, a process of silicon photolithography, whereby the engraving is done by chemical means or using a plasma, according to methods that are known to one skilled in the art.

Advantageously, according to the invention, said pressure sensor comprises at least two, and preferably four, piezoelectric transducers, placed in zones of greater deformation of the membrane.

Also according to an advantageous characteristic, said at least one piezoelectric transducer is selected from among the piezoresistive gauges, the pn-junction diodes, the bipolar transistors or the field-effect transistors. Nowadays, the resistors are the most commonly used piezoelectric element on the surface of the membranes, but any component can be used to translate a mechanical behavior of the membrane into the electrical behavior. Several gauges that have identical or different piezoresistive characteristics can be produced on the same substrate and arranged according to various configurations (assembly in a single bridge, Wheatstone bridge, etc.) improving their performance levels and reducing the impact of the influence quantities (primarily the temperature).

These gauges can be obtained by various processes. In one preferred embodiment of the device according to this invention, the piezoresistive gauges are made of doped silicon integrated into said silicon membrane. In this case, the piezoresistive gauges are not attached to the test body but are integrated into the material (here, silicon), i.e., they are constituent parts of the membrane. Actually, actuation is on an atomic level by targeted doping of the zones of the membrane where the deformations are at maximum. The doped zones transfer the pressure that is applied to the membrane by a variation of their electric characteristics. These dopings on the surface of the material can be carried out by techniques that are used in microelectronics, such as atomic diffusion or ionic implantation.

Thus, in its preferred embodiment, the implementation of the invention can advantageously be supported on the known technologies of silicon with piezoresistive transducers and on the methods for production of sensitive membranes that are developed for these purposes.

The device according to the invention may be a relative sensor. In this case, the cavity is extended by an open channel into the atmosphere.

The device according to the invention can also be an absolute sensor. In this case, in contrast, the cavity is hermetically sealed by vacuum-welding of the sensor with the actuator (this is then constituted by a conductive substrate).

According to an advantageous characteristic of the device that is the object of this invention, the latter can also comprise a temperature sensor. The latter can be produced by one of the techniques at the disposal of one skilled in the art.

For example, it may consist of a thermistor that consists of a nickel- or platinum-type metal, deposited by spraying (according to a principle widely used in Pt100- or Pt1000-type temperature sensors) or a doped semi-conductor of silicon or polysilicon, for example. This type of sensor is most often used alone, in an individual component.

Alternatively, it can consist of a silicon temperature probe with a band jump, comprising diodes or transistors through which two different currents pass and whose difference between the threshold voltages (case of the diodes) or emitter-base voltages (case of the transistors) is measured. The thus measured voltage is directly proportional to the temperature. This type of sensor, which draws its name from the reference of band-jump voltage used to generate currents passing through the diodes or the transistors, is widely used in the industry of microelectronics.

As already indicated, the piezoelectric transducers of the device according to the invention transfer the movement of the membrane induced by the electric field when the actuator is charged, in the form of an electrical signal. The latter, once processed and analyzed, will provide information on the possible drift of the sensor. For this purpose, the test body comprises, of course, means for electrical connection of the piezoelectric transducers and the polarization contact.

According to another particular characteristic of the invention, the device according to the invention is advantageously connected to a central unit that comprises means for processing the electrical signal that is generated by the pressure sensor, and optionally by the temperature sensor. The electrical signal that is generated by the piezoelectric transducers can therefore be recorded, processed and compared to values previously acquired under the same electrostatic actuation conditions to evaluate and possibly to correct a possible drift of the piezoelectric transducers, i.e., to calibrate the sensor as often as necessary. This correction is advantageously made using a suitable computer program.

The process for periodic calibration and adjustment of the value of the measured pressure can thus be produced in an automated manner by simple actuation of the only measuring device that is the object of this invention, which justifies the qualification of this self-calibrating device. This calibration makes it possible to correct—easily, instantaneously and without a health risk—the drift over time of the values of the measured intracorporeal pressure, primary weakness of the currently used pressure sensors.

For its convenient and reliable implementation in particular in medical use, the device can be attached at the end of a catheter and encapsulated in a resin sheath that comprises a window at the level of the membrane.

Finally, a catheter with a medical use whose end that is designed to be implanted in a patient's body and that comprises a self-calibrating device for measuring the intracorporeal pressure as described above is also the object of this invention.

This invention will be better understood, and details relevant thereto will be brought out in the description that will be given of various variant embodiments in relation to the figures of the accompanying sheets, in which:

DETAILED DESCRIPTION OF THE INVENTION

Example 1

Relative Sensor Combined with a Metal Electrode Actuator

Figure 1:
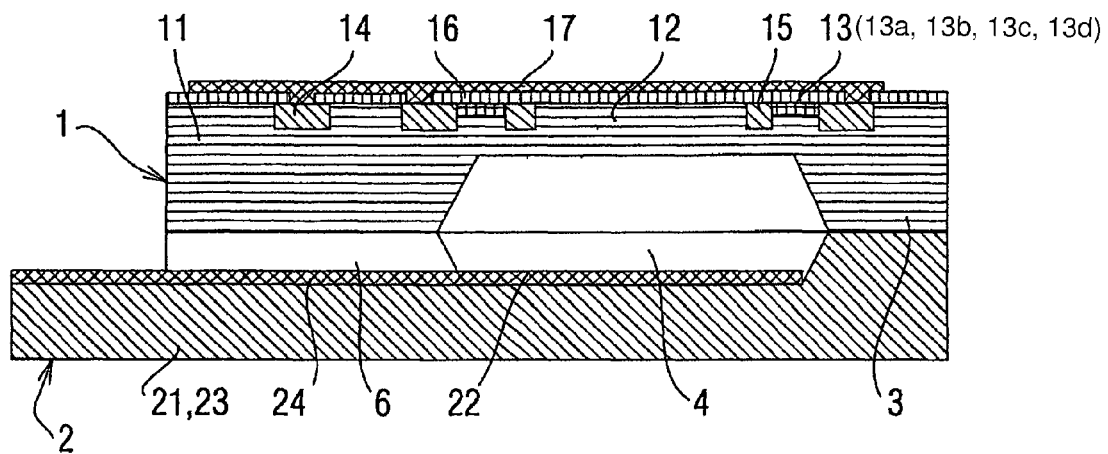
FIG. 1 is a diagrammatic cutaway representation of a device according to the invention, combining a relative sensor and an actuator that is equipped with a metal electrode on an insulating substrate.

With reference to FIG. 1, the device according to this example comprises the pressure sensor 1, which comprises, on the one hand, the test body 11, and, on the other hand, the polarization contact 14. The test body 11 has a segment of smaller thickness that constitutes the membrane 12, able to deform under the action of the pressure from the medium or from an electrostatic force. The test body 11 of the sensor 1, including the membrane 12, is made of conductive silicon.

Said membrane is equipped with four piezoelectric transducers 13, able to translate a mechanical stress into an electrical signal. The transducers 13 that are selected are piezoresistive gauges that are placed in zones of greater deformation of the membrane 12. Four gauges that are mounted on a Wheatstone bridge are used. They are integrated into the silicon membrane 12 by targeted doping of the zones where the deformations are at maximum, i.e., on each of the sides on the periphery of the membrane 12. For example, the membrane 12 is inscribed in a parallelogram that comprises a transducer 13 on each side. Strongly P++-doped interconnections 15 are provided on both sides of gauges 13. The polarization contact 14 is ensured using a strong N++ doping. The variations of the electrical characteristics of the gauges 13 transfer any movement or deformation of the membrane, caused by the pressure to be measured or by the electric field that is induced by the polarization of the assembly.

The device also comprises the actuator 2 that is connected to a voltage source, comprising the non-deformable base 21 with the polarizable surface 22. The actuator 2 consists of the non-deformable insulating substrate 23 and the metal electrode 24 that is connected to a voltage source. This metal electrode constitutes a polarizable surface of the actuator 2, placed at the base of the membrane 12. It consists of a Ti—Au or Al metal layer that covers the insulating substrate 23 over a portion of its surface, and particularly over the surface that is at the base of the membrane 12. The insulating substrate 23 is made of borosilicate glass (better known under the trade name of Pyrex™). It is this material that ensures the insulation function by separating the polarizable surface 22 and the test body 11.

The pressure sensor 1 is placed above the actuator 2 (according to the representation adopted here) so that the membrane 12 is at the base of the polarizable surface 22. It is kept at the latter by the rigid connection 3, whereby the space encompassed between the membrane 12 and the polarizable surface 22 constitutes the cavity 4 of specified size: the distance d between the electrodes is thus between 100 nm and 300 nm. The connection 3 is ensured by gluing respective extensions on the edges of the sensor 1 and the actuator 2, for example by the anodic welding technique. It does not allow the passage of the electric current. The cavity 4 is extended through the channel 6 that is open to the atmosphere. The sensor is therefore of the relative sensor type, operating by reference to the atmospheric pressure.

Figure 3:
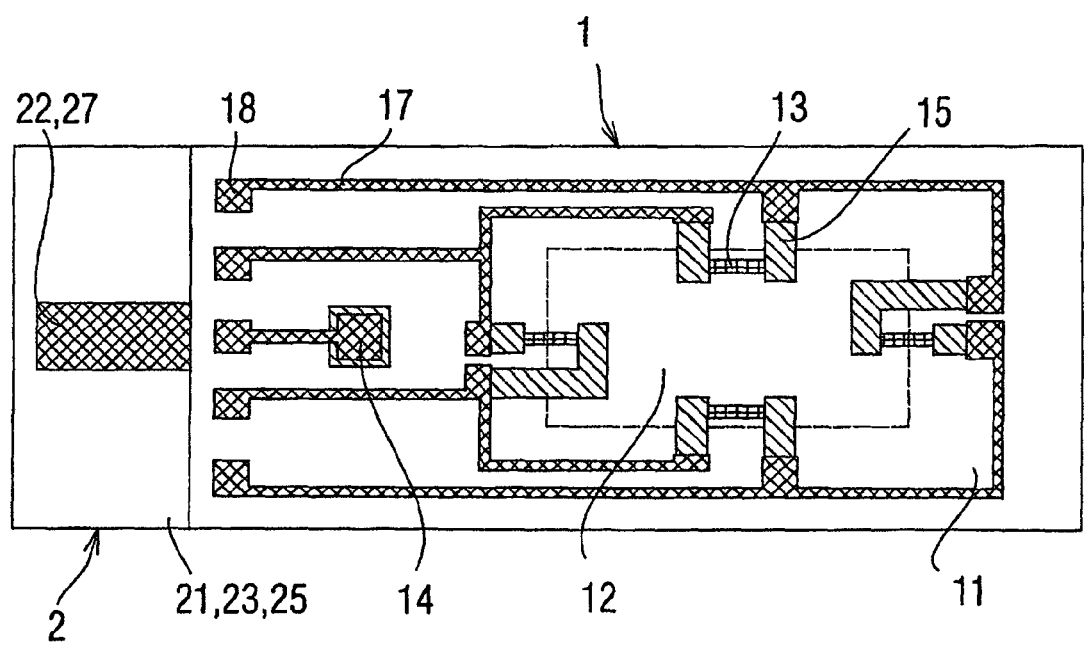
FIG. 3 is a diagrammatic top view of the devices that are shown in FIGS. 1 and 2 and that disclose only the components and the electric circuits of the sensor.

For its operation, the test body 11 comprises electrical connection means of the piezoresistive gauges 13 and the polarization contact 14. The layout of the metal tracks 17 and the connecting pins 18 is shown in FIG. 3. The metal tracks 17 are insulated from the membrane 12 by the insulating layer 16 (omitted in FIG. 3).

The production of the device that is described here makes use of known technologies that are applied to silicon with piezoelectric transducers and to methods of production of sensitive membranes that are developed for these purposes that one skilled in the art knows to select and implement.

The self-calibrating device for measuring the intracorporeal pressure can be installed at the end of a catheter. For this purpose, it can be attached to the end of a flexible strip, for example a polyimide, also supporting connection cables, and inserted into the catheter until emerging at its end. It is then encapsulated in a sheath that comprises a window at the level of the membrane. The capsule can consist in a known way of a half-cylinder into which the self-calibrating sensor slides, then it is closed by micro-deposition of a glue. The thus encapsulated device at the end of a catheter has an overall diameter on the order of 1 mm to 1.2 mm that is suitable for insertion into a patient's body.

For the production of this device, according to the following primary stages, it will be possible to initiate:
Preparation of a Pyrex™ substrate for the purpose of making a cavity with an exit channel, allowing the electrical connection of the metal electrode;
Deposition of a metal electrode on the substrate;
Production of a silicon test body with a membrane;
Implantation of piezoresistive gauges on the test body;
Implantation of P++ interconnections for the gauges and N++ for the polarization of the membrane;
Metallization for the interconnection of gauges on a Wheatstone bridge and the polarization contact of the membrane;
Welding of the actuator plate and the sensor plate for creating the cavity with two polarizable surfaces opposite one another;
Breakdown of the components.

Example 2

Absolute Sensor Combined with a Conductive Silicon Actuator

Figure 2:
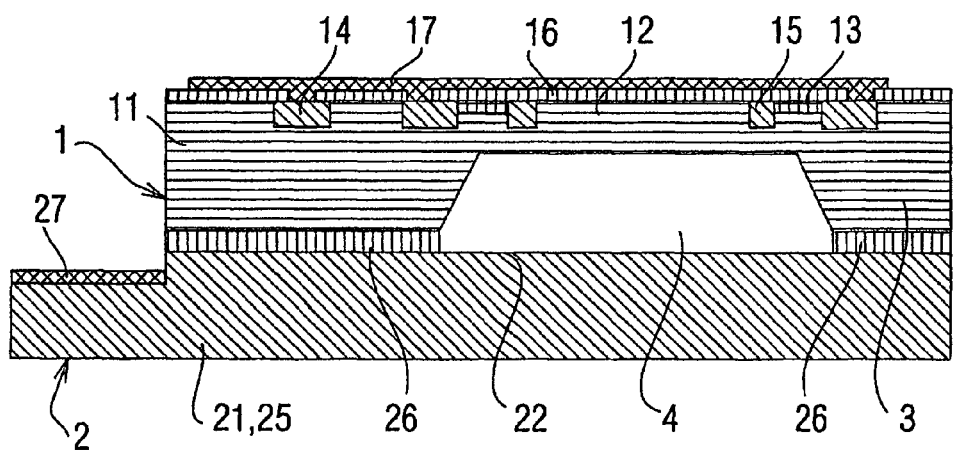
FIG. 2 is a diagrammatic cutaway view of a device according to the invention, combining an absolute sensor and an actuator comprising a conductive substrate.

With reference to FIG. 2, the device according to this example comprises the pressure sensor 1, which comprises, on the one hand, the test body 11, and, on the other hand, the polarization contact 14. The test body 11 has a segment of smaller thickness that constitutes the membrane 12, able to deform under the action of the pressure of the medium. The test body 11 of the sensor 1, including the membrane 12, is made of conductive silicon.

Said membrane is equipped with four piezoelectric transducers 13, able to translate a mechanical stress into an electrical signal. The transducers 13 that are selected are piezoresistive gauges that are placed in zones of greater deformation of the membrane 12. Four gauges are integrated into the silicon membrane 12 by targeted doping of the zones where the deformations are at maximum, i.e., on each of the sides on the periphery of the membrane 12. P++ interconnections 15 are provided on both sides of gauges 13. N++ interconnections are provided for the polarization contact 14.

The device also comprises the actuator 2 that is connected to a voltage source, comprising the non-deformable base 21 with the polarizable surface 22. The actuator 2 consists of the non-deformable conductive substrate 25 that is connected to a voltage source by a deposited metal 27 and separated from the test body 11 by the insulating element 26. The substrate 25 is a conductive silicon while the insulating element 26 is made of silicon oxide. It is this latter material that ensures the insulation function by separating the polarizable surface and the test body. The surface of the conductive substrate constitutes a polarizable surface of the actuator 2 that is placed at the base of the membrane 12.

The pressure sensor 1 is placed above the actuator 2 (according to the representation adopted here) so that the membrane 12 is at the base of the polarizable surface 22. It is kept at the latter by the rigid connection 3, whereby the space encompassed between the membrane 12 and the polarizable surface 22 constitutes the cavity 4: the distance d between the electrodes is thus set at about 1 mm. The connection 3 is ensured by gluing silicon oxide extensions at the edge of the device of the sensor 1 and the actuator 2, for example by fusion welding. It does not allow the passage of the electric current. In this case, the cavity is vacuum-sealed during welding. The sensor is therefore of the absolute sensor type.

As for the preceding example, the test body 11 comprises means for electrical connection of the piezoresistive gauges 13 mounted on the Wheatstone bridge and the polarization contact 14. The layout of the metal tracks 17 and the connecting pins 18 is shown in FIG. 3. The metal tracks 17 are insulated from the membrane 12 by the insulating layer 16 (omitted in FIG. 3). The device can be installed at the end of a catheter and encapsulated, as already described.

It is possible to produce this device according to the following primary stages:
- Production of a silicon test body with a membrane;
- Growth of an insulating oxide layer to prepare the connection with the actuator;
- Implantation of piezoresistive gauges on the test body;
- Implantation of the P++ interconnections for the gauges and N++ for the polarization of the membrane;
- Metallization for the interconnection of gauges on the Wheatstone bridge and the polarization contact of the membrane;
- Preparation of a conductive silicon plate (actuator);
- Welding of the actuator plate and the sensor plate to create a cavity with two polarizable surfaces opposite one another;
- Metallization of a portion of the actuator plate to allow the electrical connection of the plate and its polarization;
- Breakdown of the components;
- Vacuum-sealing the cavity during welding.

The invention claimed is:

1. A self-calibrating device for measuring intracorporeal pressure, comprising:
   a pressure sensor (1) comprising i) a test body (11), ii) a polarization contact (14) within the test body, iii) a membrane (12) constituted by a smaller thickness segment of the test body (11), the membrane being deformable under a pressure of a human-body medium and from an electrostatic force, and iv) a piezoelectric transducer (13) integrated into an upper surface of the membrane (12) and configured for translating a mechanical stress into an electrical signal;
   an electrostatic actuator (2) located at a base of the membrane below the sensor (1), the electrostatic actuator (2) connected to a voltage source for receiving an applied electrical voltage, the electrostatic actuator (2) comprising a non-deformable base (21) with a polarizable surface (22),
   the polarizable surface (22) being in vertical alignment with and below the membrane (12) to constitute two conductive parallel surfaces generating an electrostatic force when a potential difference is applied to the conductive parallel surfaces; and
   a cavity (4) located between a lower surface of the membrane (12) and an upper surface of the polarizable surface (22),
   wherein the electrostatic actuator (2) self-calibrates the sensor by transforming the applied electrical voltage into an electrostatic force of a known amplitude that creates a responsive deformation on the membrane, the piezoelectric transducer (13) translating mechanical stress of the responsive deformation into a responsive electrical signal corresponding to the known electrostatic force, and
   wherein, in use, the human-body medium acting on the membrane (12) causes a deformation on the membrane (12) and the piezoelectric transducer (13) translates mechanical stress of the deformation into an electrical signal.

2. The device according to claim 1, wherein,
   the sensor (1) is located above the actuator (2) by a rigid connection (3), and
   a cavity (4) of specified size is encompassed between the membrane (12) and the polarizable surface (22).

3. The device according to claim 1, wherein the actuator (2) further comprises insulating means separating the polarizable surface (22) and the test body (11).

4. The device according to claim 1, wherein the actuator (2) further comprises, on a non-deformable insulating substrate (23), a metal electrode (24) connected to the voltage source.

5. The device according to claim 4, wherein the insulating substrate (23) is a material selected from the group consisting of glass, borosilicate glass, vitreous ceramic, and insulating silicon.

6. The device according to claim 1, wherein the actuator (2) further comprises a non-deformable conductive substrate (25) connected to the voltage source and separated from the test body by at least one insulating element (26).

7. The device according to claim 6, wherein the conductive substrate (25) is made of conductive silicon, and said at least one insulating element (26) is made of silicon oxide.

8. The device according to claim 1, wherein the test body (11) and the membrane (12) of the sensor are made of conductive silicon.

9. The device according to claim 1, wherein the sensor further comprises four piezoelectric transducers (13) placed in zones of greater deformation of the membrane (12).

10. The device according to claim 1, wherein said at least one piezoelectric transducer (13) is selected from the group consisting of piezoresistive gauges (13a), pn-junction diodes (13b), bipolar transistors (13c), and field-effect transistors (13d).

11. The device according to claim 1, wherein said membrane is a silicon membrane, and wherein said at least one piezoresistive is made of doped silicon integrated into said silicon membrane.

12. The device according to claim 1, further comprising a temperature sensor.

13. The device according to claim 1, further comprising a connected central unit having electric signal processing means generated by the pressure sensor.

14. The device according to claim 1, further comprising means for attaching at the end of a catheter and wherein the pressure sensor is encapsulated in a resin sheath that has a window at the level of the membrane (12).

15. A medical catheter, wherein the end of the medical catheter is designed to be implanted in a patient's body which catheter comprises a self-calibrating device for measuring the intracorporeal pressure according to claim 1.

16. The device of claim 1, wherein,
   the piezoelectric transducer (13) comprises four piezoresistive gauges, and
   the membrane is inscribed in a parallelogram with one of the four piezoresistive gauges located on each side of a periphery of the parallelogram inscribing the membrane (12).

17. The device according to claim 2, wherein the cavity (4) is extended by an open channel (6) into an atmosphere.

18. The device according to claim 2, wherein the cavity (4) is hermetically sealed by a polymer compound (5) and the cavity is devoid of air.

19. The device according to claim 2, wherein the actuator (2) further comprises insulating means separating the polarizable surface (22) and the test body (11).

* * * * *